(12) United States Patent
Gloss et al.

(10) Patent No.: US 10,993,808 B2
(45) Date of Patent: May 4, 2021

(54) STENTED PROSTHESIS DELIVERY DEVICES HAVING STEERING CAPABILITIES AND METHODS

(71) Applicant: Medtronic, Inc., Minneapolis, MN (US)

(72) Inventors: Michael Gloss, Minneapolis, MN (US); James R. Keogh, Maplewood, MN (US); Timothy Ryan, Minnetrista, MN (US); Declan P. Costello, Galway (IE); Wayne M. Falk, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 147 days.

(21) Appl. No.: 15/916,956

(22) Filed: Mar. 9, 2018

(65) Prior Publication Data

US 2018/0256332 A1    Sep. 13, 2018

Related U.S. Application Data

(60) Provisional application No. 62/469,127, filed on Mar. 9, 2017.

(51) Int. Cl.
*A61F 2/24* (2006.01)

(52) U.S. Cl.
CPC .......... *A61F 2/2466* (2013.01); *A61F 2/2436* (2013.01); *A61F 2/2439* (2013.01); *A61F 2/243* (2013.01)

(58) Field of Classification Search
CPC ...... A61F 2/2427; A61F 2/243; A61F 2/2436; A61F 2/2439; A61F 2/2466; A61F 2/95;
(Continued)

(56) References Cited

U.S. PATENT DOCUMENTS 5,769,812 A * 6/1998 Stevens .................. A61B 17/29
   604/4.01
6,858,005 B2   2/2005 Ohline et al.
(Continued)

FOREIGN PATENT DOCUMENTS

WO    2008015257 A2    2/2008
WO    2015077229 A1    5/2015

OTHER PUBLICATIONS

Search Report and Written Opinion for related International Application No. PCT/US2018/021782 dated Jun. 6, 2018 (15 pgs.).
U.S. Appl. No. 62/469,111, filed Mar. 9, 2017 (25 pgs.).

*Primary Examiner* — Diane D Yabut
*Assistant Examiner* — Christian D Knauss
(74) *Attorney, Agent, or Firm* — Dicke, Billig & Czaja, PLLC

(57) ABSTRACT

Delivery devices and device elements that provide steering capabilities and methods of steering such delivery devices during the delivery of a stented prosthesis to a target site. Various delivery devices include a shaft assembly having a plurality of lumens through which tension members that compressively retain the stented prosthesis to the shaft assembly are routed. By selectively tensioning one or more tension members, the shaft assembly can be pulled or steered in a desired direction. Various embodiments include one or more steering or stiffening rods that can reinforce the device or counteract any unintended bending or steering of the delivery device.

19 Claims, 7 Drawing Sheets

(58) Field of Classification Search
CPC .. A61F 2/962; A61F 2/966; A61F 2002/9511; A61M 25/0071; A61M 25/0152
See application file for complete search history.

(56) References Cited

U.S. PATENT DOCUMENTS

| | | | |
|---|---|---|---|
| 8,377,113 B2* | 2/2013 | Hartley | A61F 2/95 623/1.23 |
| 2006/0264907 A1* | 11/2006 | Eskridge | A61M 25/0023 604/528 |
| 2007/0112355 A1* | 5/2007 | Salahieh | A61F 2/2418 606/108 |
| 2007/0203561 A1 | 8/2007 | Forster et al. | |
| 2008/0188928 A1* | 8/2008 | Salahieh | A61M 25/0054 623/2.11 |
| 2009/0270966 A1* | 10/2009 | Douk | A61B 17/064 623/1.11 |
| 2010/0274187 A1* | 10/2010 | Argentine | A61M 25/0082 604/96.01 |
| 2010/0286768 A1 | 11/2010 | Alkhatib | |
| 2011/0040366 A1 | 2/2011 | Goetz et al. | |
| 2012/0277734 A1 | 11/2012 | Goetz et al. | |
| 2013/0096664 A1 | 4/2013 | Goetz et al. | |
| 2013/0096670 A1 | 4/2013 | Goetz et al. | |
| 2013/0103131 A1 | 4/2013 | Goetz et al. | |
| 2013/0245752 A1 | 9/2013 | Goetz et al. | |
| 2013/0325101 A1 | 12/2013 | Goetz et al. | |
| 2013/0338755 A1 | 12/2013 | Goetz et al. | |
| 2014/0330368 A1 | 11/2014 | Gloss et al. | |
| 2015/0112430 A1 | 4/2015 | Creaven et al. | |
| 2015/0297382 A1* | 10/2015 | Tassoni, Jr. | A61F 2/966 623/1.12 |
| 2015/0351903 A1* | 12/2015 | Morriss | A61F 2/2418 623/2.11 |
| 2017/0035566 A1* | 2/2017 | Krone | A61F 2/2427 |

* cited by examiner

STENTED PROSTHESIS DELIVERY DEVICES HAVING STEERING CAPABILITIES AND METHODS

CROSS-REFERENCE TO RELATED APPLICATIONS

This Non-Provisional Patent Application claims the benefit of the filing date of U.S. Provisional Patent Application Ser. No. 62/469,127, filed Mar. 9, 2017, the entire teachings of which are incorporated herein by reference.

BACKGROUND

This disclosure relates to stented prosthesis delivery devices and device components that have steering capabilities and methods of steering such delivery devices.

A human heart includes four heart valves that determine the pathway of blood flow through the heart: the mitral valve, the tricuspid valve, the aortic valve, and the pulmonary valve. The mitral and tricuspid valves are atrio-ventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Diseased or otherwise deficient heart valves can be repaired or replaced using a variety of different types of heart valve surgeries. One conventional technique involves an open-heart surgical approach that is conducted under general anesthesia, during which the heart is stopped and blood flow is controlled by a heart-lung bypass machine.

More recently, minimally invasive approaches have been developed to facilitate catheter-based implantation of the valve prosthesis on the beating heart, intending to obviate the need for the use of classical sternotomy and cardiopulmonary bypass. In general terms, an expandable valve prosthesis is compressed about or within a catheter, inserted inside a body lumen of the patient, such as the femoral artery, and delivered to a desired location in the heart where the valve prosthesis is then deployed.

The present disclosure addresses problems and limitations relating to delivery devices, such as those of the related art.

SUMMARY

The present disclosure relates to numerous delivery devices for delivering a stented prosthesis including, but not limited to, stented prosthetic heart valves or coronary prosthesis, endoprosthesis, peripheral prosthesis, gastric devices or the like. Such delivery devices can include an optional outer sheath assembly, a shaft assembly for supporting the stented prosthesis and a handle assembly. The delivery device provides a loaded delivery state in which the stented prosthesis is loaded and compressed over the shaft assembly. The compression of the stented prosthesis can be adjusted with one or more tension members (e.g., sutures, cords, wires or filaments), which extend around the stented prosthesis and proximally to an actuation and release assembly, which can, in some embodiments, be provided in the handle assembly. The delivery device can be manipulated to adjust tension in the tension members to permit the stented prosthesis to self-expand, contract and ultimately release from the shaft assembly.

Embodiments disclosed herein further utilize tension members, routed through one or more lumens in the shaft assembly, to steer the delivery device during delivery of the stented prosthesis (e.g., to bend the shaft assembly through the aortic arch or to impact coaxiality of the stented prosthesis at a canted native heart valve). One or more steering or stiffening rods can also be used to assist in reinforcing or stiffening the shaft assembly and/or assist in steering the delivery device. The shaft assembly includes one or more lumens through which the tension members and optional steering or stiffening rods are received. To "steer" and direct a distal end of the delivery device, tension is applied to one or more respective tension members to subsequently shorten the respective length of tension member within the shaft assembly, which effectively pulls and bends the shaft assembly to a side of the shaft assembly in which the tensioned tension member is positioned. In addition, steering with one or more steering or stiffening rods can be accomplished by inserting one or more rods into lumens of the shaft assembly to straighten the shaft assembly. In some embodiments, one or more lumens are provided in the outer sheath assembly to receive a respective rod to assist in reinforcing or stiffening the outer sheath assembly and/or assist in steering the delivery device. Steering control of the tension members and/or rods can be manual or motorized, as desired.

DETAILED DESCRIPTION

Specific embodiments of the present disclosure are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

Figure 1:
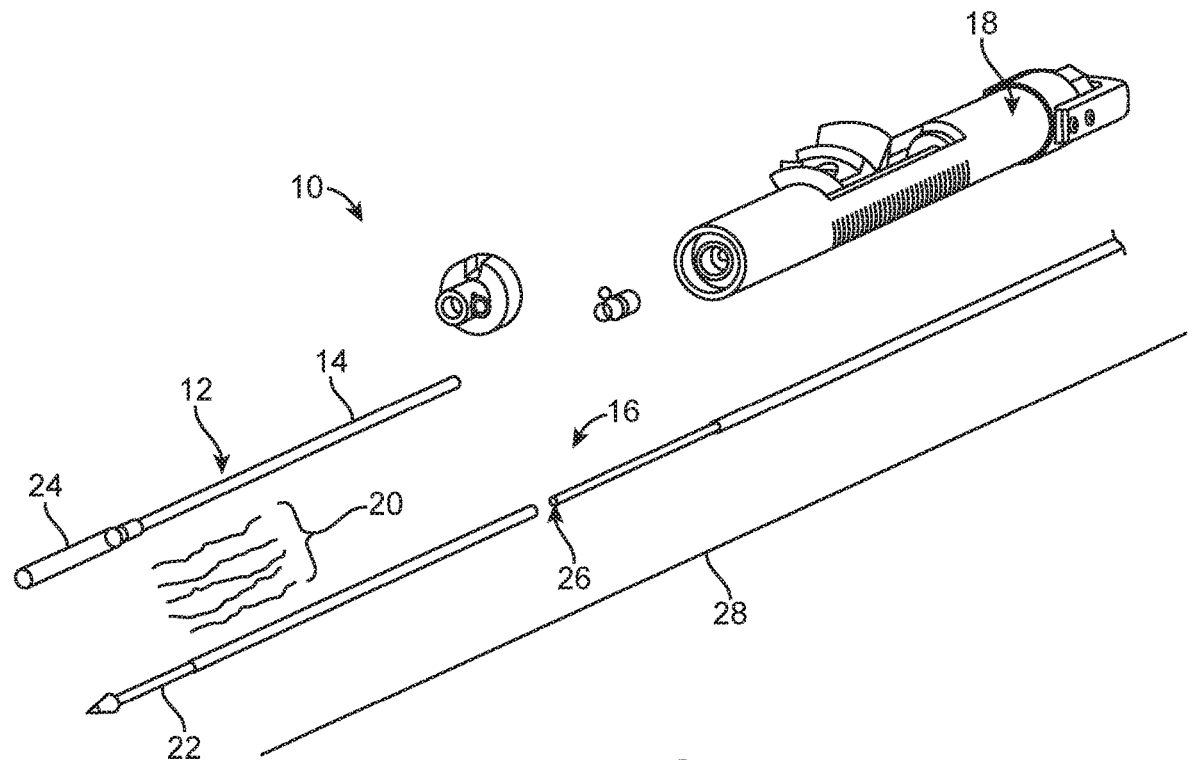
FIG. 1 is a perspective view of an example of a delivery device for delivering a stented prosthesis.
Figure 2A:
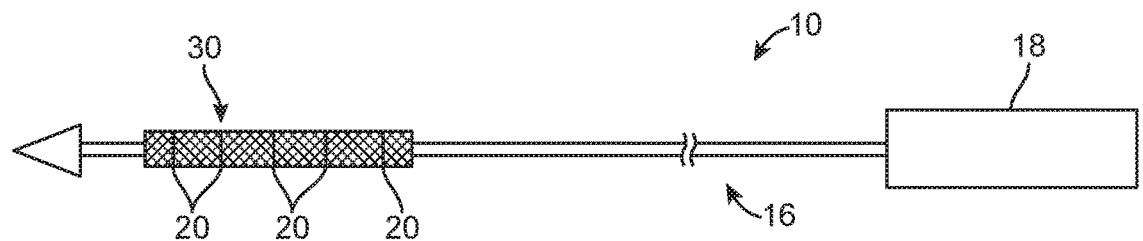
FIG. 2A is a schematic illustration of the delivery device of FIG. 1 having the stented prosthesis positioned over a shaft assembly of the delivery device in a compressed arrangement with a plurality of tension members.
Figure 2B:
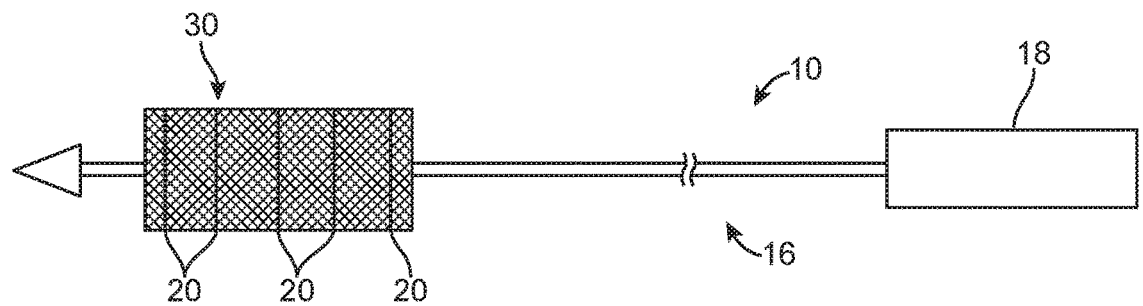
FIG. 2B is a schematic illustration of the delivery device of FIG. 2A having the stented prosthesis positioned over the shaft assembly of the delivery device in an expanded arrangement with the plurality of tension members.
Figure 3:
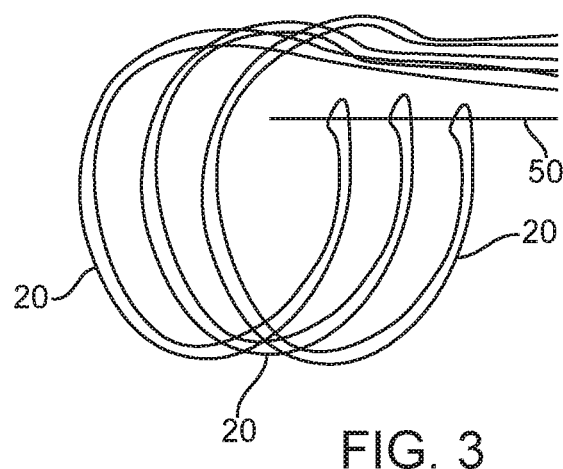
FIG. 3 is a schematic illustration of one or many ways in which tension members can be maintained with a release pin and wrapped around the stented prosthesis (the stented prosthesis is not shown for ease of illustration).

As described below, some aspects of the present disclosure relate to delivery devices utilizing one or more tension members to compress and retain a stented prosthesis during transcatheter delivery to a target site. By way of background, general components of one non-limiting example of a delivery device 10 with which some aspects of the present disclosure are useful are illustrated in FIGS. 1-3. The delivery device 10 is arranged and configured for percutaneously delivering a stented prosthesis, such a stented prosthetic heart valve 30 (schematically illustrated), to a target site. The delivery device 10 includes an optional outer sheath assembly 12 having a flexible outer sheath 14, a flexible shaft assembly 16 and a handle assembly 18. The shaft assembly 16 can include a distal portion 22 and define a continuous lumen 26 (referenced generally) sized to slidably receive an auxiliary component such as a guide wire 28. In this embodiment, the outer sheath 14 is interconnected to a capsule 24 that is selectively disposed over the stented prosthesis 30 and assists in constraining the stented prosthesis 30 in the compressed arrangement. The capsule 24 can be retracted by the handle assembly 18 to expose the stented prosthesis 30 for deployment.

One or more tension members 20 (e.g., sutures, cords, wires or filaments) are further provided, and can be considered part of the delivery device 10 in some embodiments or as part of the stented prosthesis 30 in other embodiments. Examples in which the tension members 20 can be arranged are schematically illustrated in FIGS. 2A-3 (the stented prosthesis and other delivery device components being omitted in FIG. 3 for ease of illustration). One end of each of the tension members 20 can be secured proximate the handle assembly 18, then each tension member 20 can extend distally to wrap around the stented prosthesis 30 positioned over the distal portion 22 to a release pin 50 positioned adjacent the stented prosthesis 30 and then back to the handle assembly 18 or other mechanism for maintaining and adjusting the desired level of tension in the tension members 20 either individually or in pairs or groups of tension members. Other tension member arrangements are envisioned. The delivery device 10 provides a loaded, compressed arrangement (FIG. 2A) in which the stented prosthesis 30 is loaded over the shaft assembly 16 and is compressively retained on the distal portion 22 by the tension members 20. As is schematically illustrated in FIGS. 2A-2B, compression of the stented prosthesis 30 is adjustable with the tension members 20. In this illustrated embodiment, the tension members 20 wrap around the stented prosthesis 30 normal to an axis of the shaft assembly 16. Alternatively, the tension members 20 can be configured to wrap around the stented prosthesis 30 at other angles with respect to the axis of the shaft assembly 16.

After being loaded, compressed and optionally sheathed with the capsule 24, the stented prosthesis 30 is delivered to the native defective heart valve. Once the stented prosthesis 30 is sheathed with the capsule 24, tension in the tension members 20 can be released, if desired, as the capsule 24 maintains the stented prosthesis 30 in the compressed arrangement. Once in position, the capsule 24 is retracted (if provided) and/or tension in the tension members 20 is lessened or released to permit the stented prosthesis 30 to self-expand to an expanded arrangement, partially releasing and ultimately fully deploying the stented prosthesis 30 from the shaft assembly 16 (see, FIG. 2B). Then, the release pin 50 is proximally retracted to disengage from the tension members 20 so that the tension members 20 can be released from the stented prosthesis 30 and withdrawn from the patient along with the delivery device 10. In alternate embodiments, the release pin 50 is omitted and the tension members 20 can be cut for release from the stented prosthesis 30. The present disclosure focuses on numerous ways to steer a delivery device, such as the delivery device 10, during delivery of the stented prosthesis 30, which can be particularly useful when navigating the delivery device around a patent's aortic arch to avoid vessel trauma. It is to be understood that the delivery device disclosed above is provided as only one example and that aspects of the disclosure can also be used with minimally invasive surgical devices that are delivered without the use of tension members. Moreover, aspects of the present disclosure can also be used with transcatheter prosthetic valves where the delivery is accomplished in multiple steps (i.e. first deploying a stent or dock with a skirt and then delivering a valve inside the implanted dock).

As referred to herein, stented prostheses useful with the various devices and methods of the present disclosure may assume a wide variety of configurations. For example, the stented prosthesis can be a bioprosthetic heart valve having tissue leaflets or a synthetic heart valve having polymeric, metallic or tissue-engineered leaflets, and can be specifically configured for replacing valves of the human heart. The stented prostheses of the present disclosure may include sent frames that are self-expandable, balloon expandable and/or mechanically expandable or combinations thereof. In general terms, stented prosthetic heart valves of the present disclosure include a stent or stent frame having an internal lumen maintaining a valve structure (tissue or synthetic), with the stent frame having a normal, expanded condition or arrangement and collapsible to a compressed condition or arrangement for loading within the delivery device. The stents or stent frames are support structures that comprise a number of struts or wire segments arranged relative to each other to provide a desired compressibility and strength to the prosthetic valve. The struts or wire segments are arranged such that they are capable of self-transitioning from, or being forced from, a compressed or collapsed arrangement to a normal, radially expanded arrangement. The struts or wire segments can be formed from a shape memory material, such as a nickel titanium alloy (e.g., Nitinol™). The stent frame can be laser-cut from a single piece of material, or can be assembled from a number of discrete components.

One non-limiting example of a stented prosthesis is the stented prosthetic heart valve 30 (hereinafter "prosthetic valve") illustrated in FIGS. 4A-4B. As a point of reference, the prosthetic valve 30 is shown in a normal or expanded arrangement in the view of FIG. 4A and a compressed arrangement in FIG. 4B. The prosthetic valve 30 includes a stent or stent frame 32 and a valve structure 34. The stent frame 32 can assume any of the forms mentioned above, and is generally constructed to be self-expandable from the compressed arrangement to the normal, expanded arrangement. As discussed above, compression of the prosthetic valve 30 can be achieved with one or more tension members 20.

The valve structure 34 of the prosthetic valve 30 can assume a variety of forms, and can be formed, for example, from one or more biocompatible synthetic materials, synthetic polymers, autograft tissue, homograft tissue, xenograft tissue, or one or more other suitable materials. In some embodiments, the valve structure 34 can be formed, for example, from bovine, porcine, equine, ovine and/or other suitable animal tissues. In some embodiments, the valve structure 34 is formed, for example, from heart valve tissue, pericardium, and/or other suitable tissue. In some embodiments, the valve structure 34 can include or form one or more leaflets 36. For example, the valve structure 34 can be in the form of a tri-leaflet bovine pericardium valve, a bi-leaflet valve, or another suitable valve.

Figure 4A:
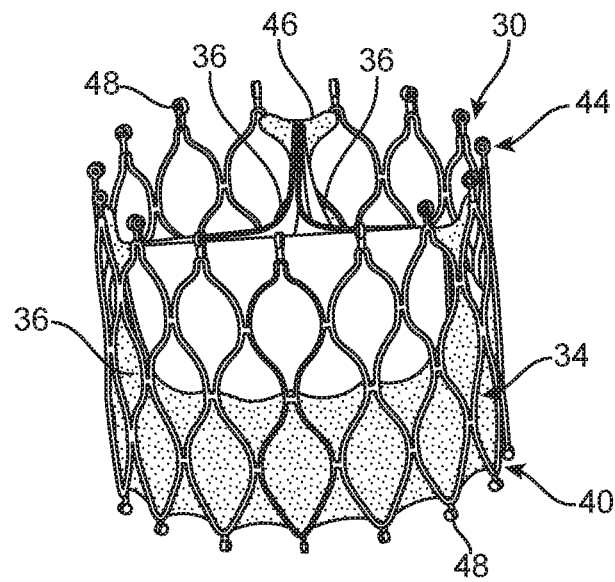
FIG. 4A is a perspective view of a stented prosthetic heart valve, which can be used with the delivery devices disclosed herein, shown in the expanded arrangement.
Figure 4B:
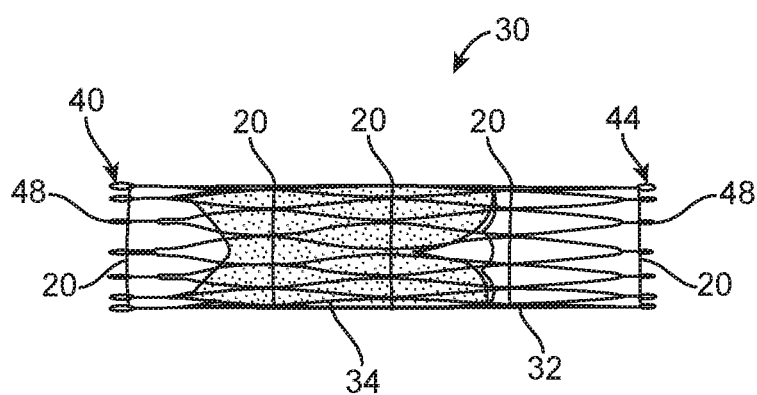
FIG. 4B is a front view of the stented prosthetic heart valve of FIG. 4A in a compressed arrangement.

In some prosthetic valve constructions, such as that of FIGS. 4A-4B, the valve structure 34 can comprise two or three leaflets 36 that are fastened together at enlarged lateral end regions to form commissural joints, with the unattached edges forming coaptation edges of the valve structure 34. The leaflets 36 can be fastened to a skirt that in turn is attached to the stent frame 32. The prosthetic valve 30 includes a first end 40 and an opposing second end 44 of the prosthetic valve 30. As shown, the stent frame 32 can have a lattice or cell-like structure, and optionally forms or provides posts 46 corresponding with commissures of the valve structure 34 as well as features 48 (e.g., crowns, eyelets or other shapes) at the first and second ends 40, 44. If provided, the posts 46 are spaced equally around the stent frame 32 (only one post 46 is clearly visible in FIG. 4A).

Figure 5:
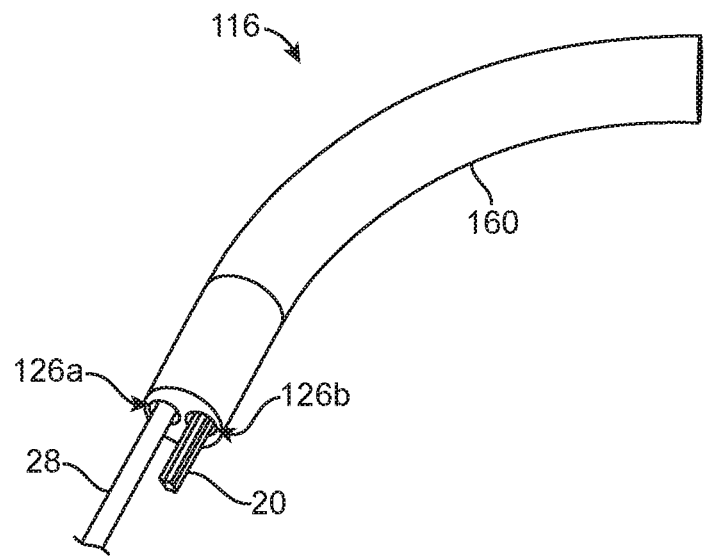
FIG. 5 is a perspective view of select components of an alternate delivery device including a shaft assembly having two lumens (the shaft assembly is shown as truncated for ease of illustration).

Turning now also to FIG. 5, which schematically illustrates select components of a delivery device 110 that is largely similar to the delivery device 10 of FIGS. 1-3 except as explicitly stated. In this embodiment, a shaft assembly 116 (which is truncated for ease of illustration) is configured to have two lumens 126a, 126b on opposite sides along the diameter of the shaft assembly 116. In one lumen 126a, a guide wire 28 is positioned. In the second lumen 126b, one or more tension members 20 are threaded from the proximal end of the delivery device (e.g., from the handle assembly 18 or the like), through the shaft assembly 116 to and around a stented prosthesis positioned on the shaft assembly (e.g., on the distal portion 22) and then back down to the proximal end of the delivery device 110. During delivery of the stented prosthesis, the capsule can optionally be secured over the crimped valve to maintain the prosthetic valve in a compressed condition (see also, the prosthetic valve 30 and capsule 24 disclosed previously). Then, tension in the tension members 20 can be eased or entirely released. When steering of the delivery device 110 is desired during delivery of the stented prosthesis one or more of the tension member(s) 20 can be pulled proximally, which will result in the shaft assembly 116 bending toward the side of the shaft assembly 116 on which the tension member(s) 20 are positioned (i.e. in the direction of the second lumen 126b as is shown in FIG. 5). Bending of the shaft assembly 116 creates a smallest arch angle 160 proximate the second lumen 126b that houses the tensioned tension member(s) 20. In this way, the tension member(s) 20 are used for both compressing the stented prosthesis as well as bending the shaft assembly 116, which provides a steering capability of the delivery device 110.

Figure 6:
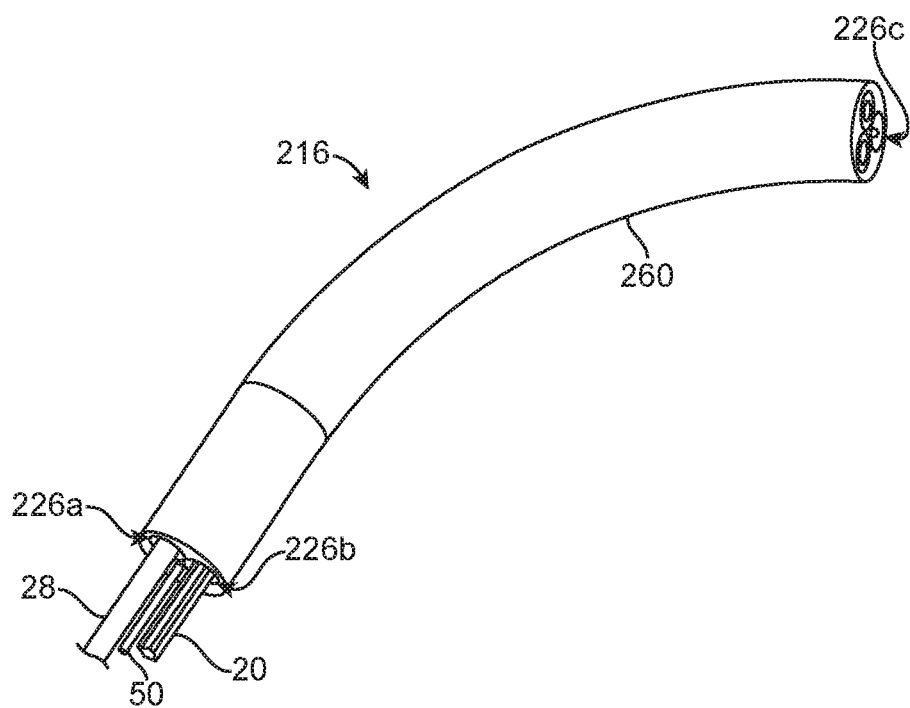
FIG. 6 is a perspective view of select components of an alternate delivery device including a shaft assembly having three lumens through which one or more tension members can be routed (the shaft assembly is truncated for ease of illustration).

A truncated alternate shaft assembly 216, which can be used as a replacement for any of the above-disclosed shaft assemblies, is illustrated in FIG. 6, which includes first, second and third lumens 226a-c. Optionally, the lumens 226a-c can be equally sized and/or symmetrically arranged within the shaft assembly 216. The first lumen 226a can receive a guide wire 28, the second lumen 226b can house one or more tension members 20 and the third lumen can receive the release pin 50, if provided. Similar to the prior disclosed embodiment, the tension members 20 can be tensioned to steer the delivery device in the direction of the second lumen 226b. As the tension members 20 are pulled proximally, the length of the tension member(s) 20 shortens, thus correspondingly bending the shaft assembly 216 to have a smallest arch angle 260 proximate the second lumen 226b.

Figure 7A:
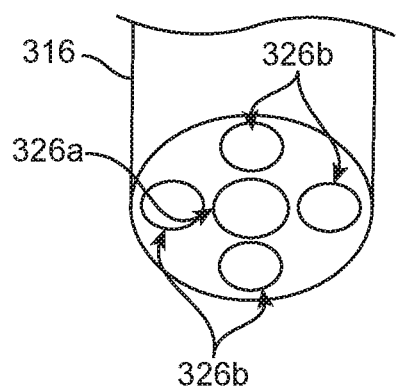
FIG. 7A is a perspective view of an alternate a shaft assembly having four outer lumens surrounding a central lumen; wherein one or more tension members can be routed through the outer lumens (the tension members are not shown and the shaft assembly is truncated for ease of illustration).
Figure 7B:
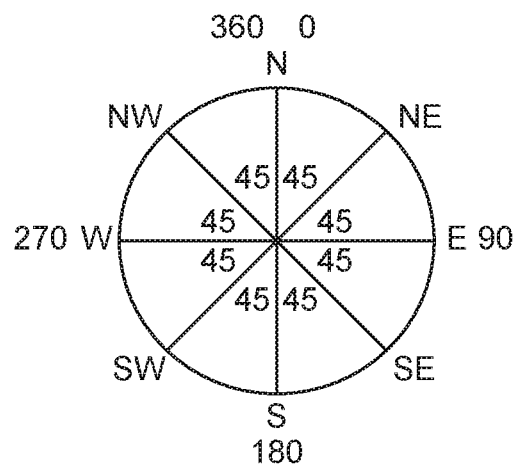
FIG. 7B is a diagram illustrating the directions in which the shaft assembly of FIG. 7A can be steered.

Turning now also to FIG. 7A, which illustrates a truncated alternate shaft assembly 316 including a central lumen 326a surrounded by four outer lumens 326b. In the illustrated embodiment, which can be a substitute for any of the above-disclosed shaft assemblies, the outer lumens 326b are equally sized and symmetrically spaced about the central lumen 326a, however, equal sizing and symmetric spacing is not required. In various embodiments, a guide wire (e.g., guide wire 28 of FIG. 1) is received within the central lumen 326a and one or more tension members are threaded through one or more of the outer lumens 326b, as desired. The arrangement of tension members (not shown, see also FIGS. 5-6) within the outer lumens 326b is selected to provide the desired steering capabilities. For example, if at least one tension member is positioned in each outer lumen 326b, the shaft assembly 216 can be steered in four directions by tensioning respective tension members within one outer lumen 326b. See FIG. 7B, for example, which helps illustrate that if tension members are threaded through each of the outer lumens 326b of FIG. 7A, the shaft assembly 316 can be steered "North", "East", "South" and "West" (i.e. 0 degrees, 90 degrees, 180 degrees, 270 degrees). It may be also desirable to tension two adjacent tension members, thus providing an additional four directions of steering capability (e.g., "Northeast" 45 degrees, "Southeast" 135 degrees, "Southwest" 225 degrees and "Northwest" 315 degrees).

Figure 8:
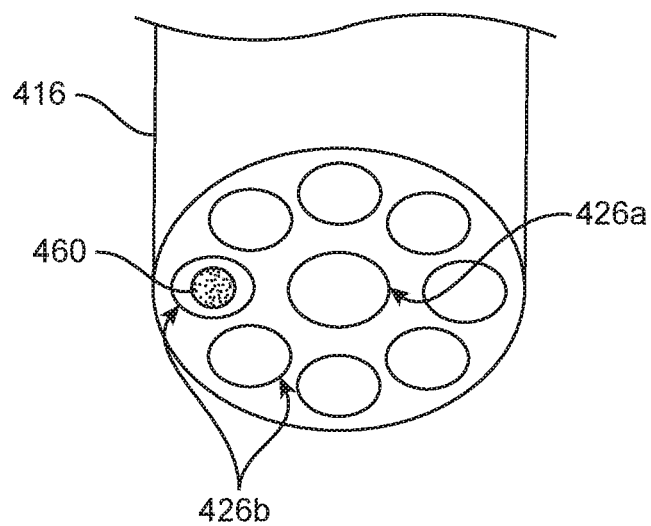
FIG. 8 is a perspective view of select components of an alternate delivery device including a shaft assembly having eight outer lumens surrounding a central lumen; wherein a rod is positioned within one of the outer lumens and one or more tension members can be routed through the outer lumens (the tension members are not shown and the shaft assembly is truncated for ease of illustration).

Alternatively, fewer or more external lumens can be provided. For example, FIG. 8 illustrates a similar truncated shaft assembly 416 having one central lumen 426a surrounded by eight outer lumens 426b that are optionally equally sized and symmetrically spaced therearound (only a few of which are labeled for ease of illustration). A guide wire (e.g., guide wire 28) can be received in the central lumen 426a and one or more tension members can be routed through the outer lumens 426b (tension members not shown for ease of illustration, see also, FIGS. 5-6). If select tension member(s) routed through one of the outer lumens 426b are tensioned, the shaft assembly 416 will bend and define a smallest arch angle of the shaft assembly 416 proximate respective outer lumen 426b housing the tensioned tension member(s). It is also possible to keep the possible number of steering directions less complex and to provide fewer steering direction options. In such an embodiment, multiple adjacent tension members can be configured to be pulled or tensioned simultaneously. As will be understood, the shaft assembly 416 can be used in place of any of the shaft assemblies disclosed herein.

As generally depicted in FIG. 8, all embodiments disclosed herein can optionally include one or more steering or stiffening rods 460 that have a stiffness greater than that of the material of the shaft assembly 416 can be inserted into one or more of the outer lumens 426b to further aid in steering and/or stiffening the delivery device (e.g., delivery device 10). For example, to counteract the tension member steering or correct other undesired bending of the shaft assembly 416, a steering or stiffening rod 460 can be pushed distally through at least one respective outer lumen 426b to stiffen and straighten the shaft assembly 416. The amount or degree of bending and the location of bending along the shaft assembly 416 can be varied by controlling the amount the one or more steering or stiffening rods 460 are moved distally or proximally within the respective outer lumens 426b. One or more steering or stiffening rods 460 can be positioned between a proximal position and a distal position to straighten the length of the shaft assembly 416 at the location(s) in which the one or more steering or stiffening rods 460 are distally or proximally positioned. In alternate embodiments, the release pin 50 can also be arranged and configured to function as a steering or stiffening rod. In such embodiments, the release pin 50 can be positioned from a proximal position to a distal position to straighten the length of the shaft assembly 416 at the location(s) in which the release pin 50 is distally advanced. In further embodiments, the release pin 50 can be tubular and a steering rod 460 can be pushed therethrough to straighten the shaft assembly 416 at the locations in which the steering rod 460 is inserted. Therefore, the steering or stiffening rod embodiments disclosed herein are useful with delivery devices utilizing tension members for steering or delivery devices that do not utilize tension members for steering purposes.

Figure 9:
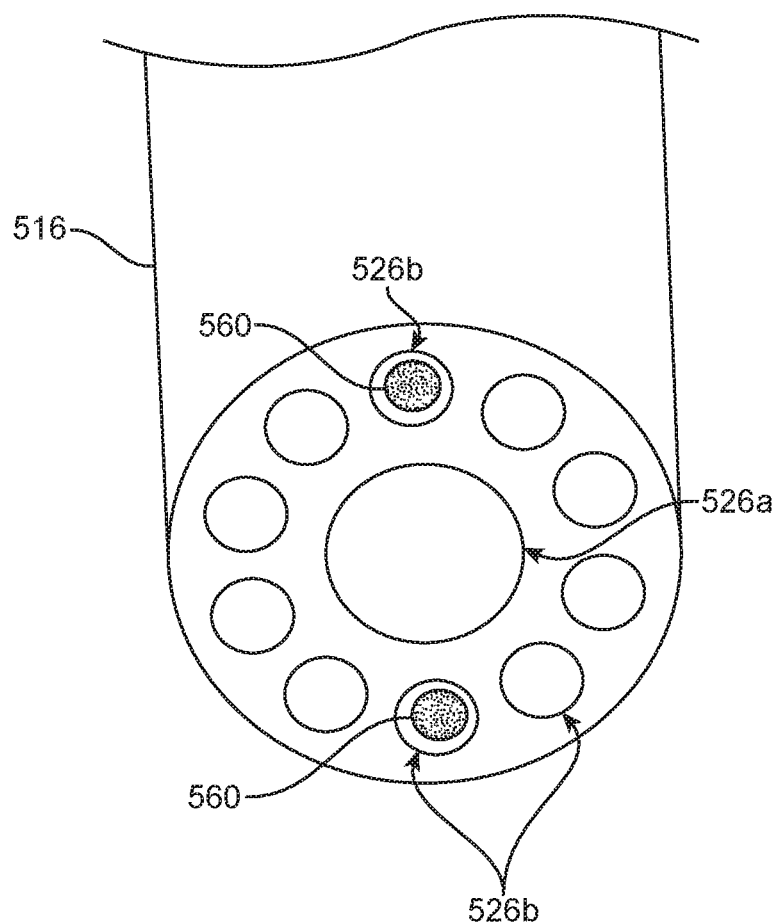
FIG. 9 is a perspective view of select components of an alternate delivery device including a shaft assembly having ten outer lumens surrounding a central lumen; wherein two rods can be selectively positioned within respective outer lumens and one or more tension members can be routed through the outer lumens (the tension members are not shown and the shaft assembly is truncated for ease of illustration).

It is further envisioned that a plurality of steering or stiffening rods can be used. Referring now also to FIG. 9, which illustrates a truncated alternate shaft assembly 516 having a central lumen 526a through which a guide wire (e.g., guide wire 28) can be received. Surrounding the central lumen 526a are ten outer lumens 526b that are optionally generally uniform in size and evenly spaced around the central lumen 526a. One or more tension members can be threaded through all or fewer than all of the outer lumens 526b (tension members not shown for ease of illustration, see also FIGS. 5-6). In this embodiment, two or more steering or stiffening rods 560 are provided, which can be inserted into respective outer lumens 526b or the like to straighten and steer the shaft assembly 516, as desired. Steering of the shaft assembly 516 can be accomplished in similar ways disclosed above with respect to prior embodiments.

Figure 10:
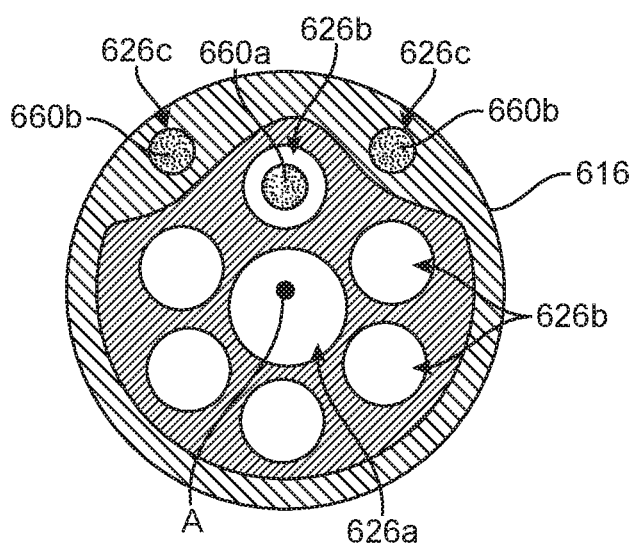
FIG. 10 is a cross-sectional view of an alternate shaft assembly having asymmetrically placed lumens with respect to a central axis of the shaft assembly.

Turning now also to FIG. 10, which illustrates the cross-section of an alternate shaft assembly 616 that can be used as an alternative for any shaft assembly disclosed herein. The shaft assembly 616 includes a lumen 626a, which is surrounded by a plurality of lumens 626b (only a few of which are referenced for ease of illustration). In this embodiment, the lumens 626a-b are offset and asymmetrical with respect to a central axis A of the shaft assembly 616. It will be understood that this is one example of how the lumens 626a-b can be arranged and configured and that any of the above-referenced embodiments can be similarly arranged to be off-center and asymmetrical. Similar to prior embodiments, one or more steering or stiffening rods 660a having a stiffness greater than that of the material of the shaft assembly 616 can be inserted within the lumens 626a-b to steer or straighten the inner shaft 616 in the manner described above with respect to the embodiments. The shaft assembly 616 can also include one or more optional steering or stiffening rods 660b positioned in respective lumens 626c, which extend through a portion or entire length of the shaft assembly 616. The steering or stiffening rods 660b have a stiffness greater than that of the material of the shaft assembly 616 and the rods 660b can either be permanently fixed within the shaft assembly 616 to provide stiffening, alignment and support to the shaft assembly 616 or, alternately, the steering or stiffening rods 660b can be removably insertable within their respective lumens 626c.

Figure 11:
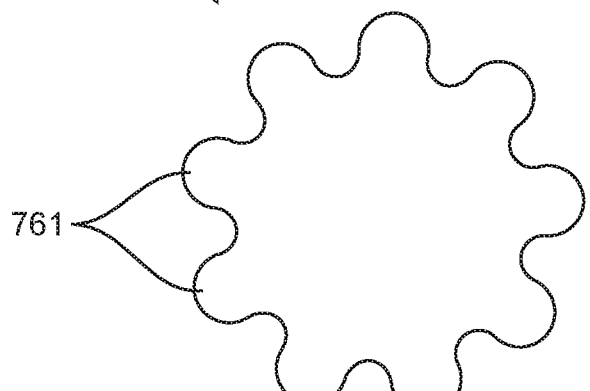
FIG. 11 is an end view of an alternate rod.

The steering or stiffening rods disclosed herein can take a variety of shapes. In many of the embodiments disclosed above, the rods have a flexible cylinder or wire form configuration. In alternate embodiments, such as that shown in FIG. 11, a steering or stiffening rod 760 can have a cross-section defining a plurality of radially-extending supports 761 (only a few of which are referenced for ease of illustration). In other words, the illustrated embodiment is configured to include a cross-section or end view having sinewave imposed on the radius of a circle. The embodiment of FIG. 11 is beneficial in that the supports 761 provide reduced surface contact between the surface of the rod and the surface of the respective lumen (e.g., any lumen disclosed herein) as compared to a cylindrical rod, which makes it easier to slide the steering or stiffening rod 760 within the respective lumen. Other support 761 configurations are also envisioned.

To further reduce friction between a lumen and any element inserted therein, any of the shaft assembly lumens disclosed herein can optionally be configured to include a coating or insert sleeve (not visible). The coating or insert sleeve can be a low-friction coating or insert sleeve comprising one or more materials such as high-density polyethylene (HDPE), polytetrafluoroethylene (PTFE) or the like to ease insertion of any disclosed rods or tension members. The coating or insert sleeve can cover all of part of the surface defining the lumen, as desired.

Figure 12:
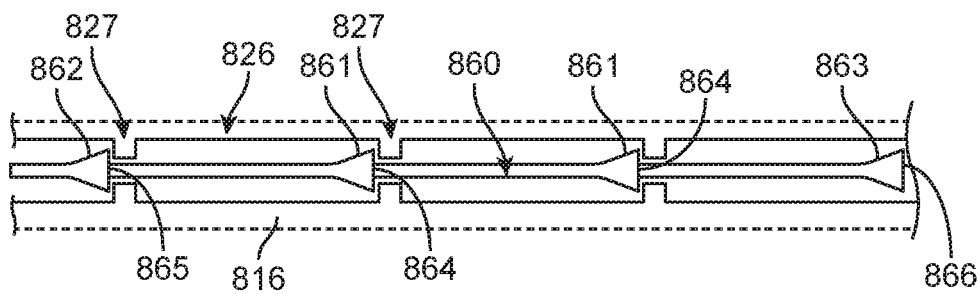
FIG. 12 is a cross-sectional view of a one way rod and lumen configuration.

Turning now also to FIG. 12, which illustrates an alternate lumen 826 and a steering or stiffening rod 860, which are collectively configured to provide a steering or stiffening rod 860, which is restricted to unidirectional movement within the lumen 826. In this embodiment, the lumen 826 is configured to define a plurality of ridges or protrusions, 827 (only a few of which are referenced) that narrow a diameter of the lumen 826 along a length of the lumen at the protrusions 827. Therefore, the lumen 826 has a varying internal diameter along at least a portion of its length. The rod 860 is configured to include a plurality of protrusions 861, positioned between a distal protrusion 862 and a proximal protrusion 863. The rod protrusions 861, 862, and 863 can be generally conical in shape so that the rod 860 can be pushed distally past the lumen protrusions 827 to advance the rod 860 but the lumen protrusions 827 will catch on circular end surface 864, 865, 866 of the rod protrusions 861, distal protrusion 862 and proximal protrusion 863, respectively, if the rod 860 is urged in the proximal direction.

Figure 13:
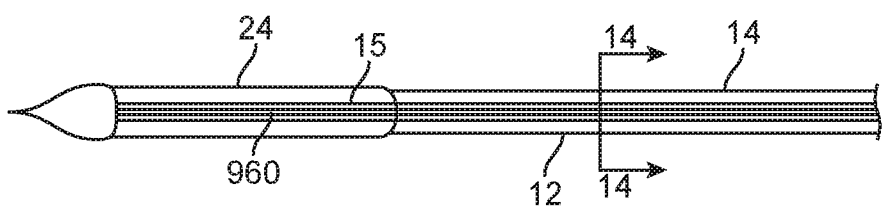
FIG. 13 is a schematic side view of the outer sheath assembly of FIG. 1 configured such that the outer sheath assembly includes one or more lumens through which respective rod(s) can be positioned (an outer sheath and capsule are shown as transparent for ease of illustration)
Figure 14:
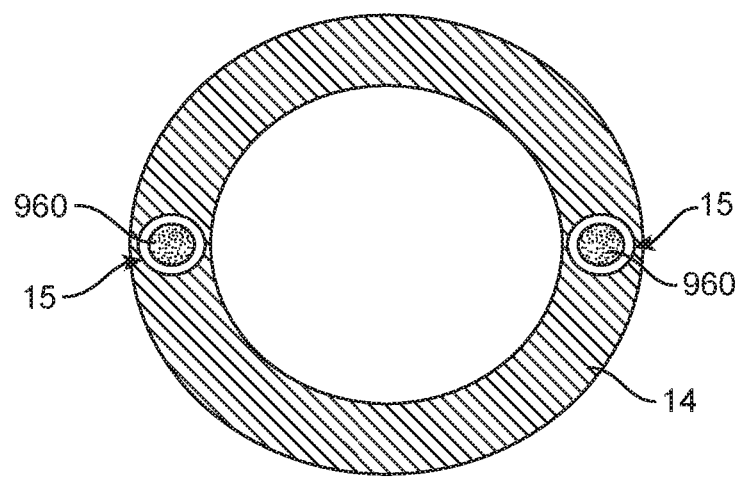
FIG. 14 is a cross-sectional view of the outer sheath assembly of FIG. 13 as viewed from line 14-14.

Turning now also to FIGS. 13-14, which collectively illustrate the outer sheath assembly 12 of FIG. 1 configured to receive one or more steering or stiffening rods 960 via lumens 15 provided within the outer sheath assembly 12 (the outer sheath 14 and capsule 24 are shown as transparent for ease of illustration). Two lumens 15 are illustrated in FIG. 14, however, it will be understood that fewer or more lumens can be provided and the lumens 15 can be positioned in different circumferential locations in the capsule 24 and/or outer sheath 14, as desired. Each steering or stiffening rod(s) 960 can be selectively inserted within one respective lumens 15 to increase the strength and support the capsule 24 for loading or recapture of the stented prosthesis, for example. The rod(s) 960 can be distally advanced and/or proximally retracted within respective lumens 15, as desired, to allow for selective stiffening of portions of the outer sheath assembly 12. The rod(s) 960 and lumen(s) 15 can take the configuration of any rod and lumen disclosed herein with respect to other embodiments. For example, the lumen(s) 15 can optionally include a coating or insert sleeve to reduce friction, as discussed above. It will further be understood that when the outer sheath assembly 12 is provided, tension members 20 are optional and may not be required to adequately compress the stented prosthesis for delivery (see also, FIG. 1). It will further be understood in view of this disclosure that although the outer sheath assembly 12 is described in the context of use with the delivery device 10 of FIG. 1, the outer sheath assembly 12 described with respect to FIGS. 13-14 can be used with other delivery devices.

All embodiments disclosed herein can optionally be steered by sequentially releasing or tightening the one or more tension members in order to retain a particular orientation. In addition, all of the disclosed embodiments can include one or more additional tension members running through the central lumen in various points that would either attach to the stent frame (e.g., eyelet) or a distal tip of the delivery device. This optional configuration would allow the user to steer the stented prosthesis to a desired orientation. In such embodiments, the tension members can be wrapped around the stented prosthesis at various angles with respect to a central axis of the shaft assembly to accomplish desired steering capabilities.

The number of lumens in the shaft assembly for receiving one or more tension members, release pins and/or steering or stiffening rods or the like can, in some embodiments, be dictated by the number of tension members circumscribing the stented prosthesis. For example, in one example embodiment, three tension members circumscribe the stented prosthesis and three outer lumens can be provided in the shaft assembly such that each tension member tracks up to the stented prosthesis and the back down a single lumen. In other embodiments utilizing three tension members, six lumens can be provided in the shaft assembly such that each tension member is maintained in two lumens, one for a first length of tension member extending to the stented prosthesis and one adjacent lumen for a second length of a tension member extending from the stented prosthesis back toward the handle assembly. Similarly, four tension members can be managed with either four or eight lumens provided in the shaft assembly, and so on. The disclosure is not intended to be limited to any number of tension members, lumens or steering or stiffening rods utilized nor is the disclosure intended to be limited to any specific arrangement thereof within a shaft assembly.

The disclosed embodiments can be motorized to control the steering of one or more tension members and/or rods. By controlling the tension of each tension member and the movement of each rod with one or more motors motor, a user interface for steering can be simplified, which may be particularly desirable in embodiments having a large number of actuators for controlling the tensioning of each tension member and/or movement of each steering or stiffening rod. In further embodiments, a joystick or the like can be utilized to direct and control a 360 degree steering range of the shaft assembly.

Further embodiments can include a device to limit the amount of tension that can be applied to the tension members to prevent damage to the device, which could compromise the procedure. Such tension limiting devices can include a drag washer system, similar to that used in fishing reels or the tension management devices disclosed in U.S. Patent Application Ser. No. 62/469,111 filed Mar. 9, 2017, the disclosure of which is hereby incorporated by reference herein in its entirety. In further various embodiments, a motor of the handle assembly that powers an actuator that controls movement of the tension members, rod and, perhaps, other components of the delivery device, can be used to limit tension by utilizing a voltage sensor or by implementing a load cell on the actuator, for example.

Although the present disclosure has been described with reference to preferred embodiments, workers skilled in the art will recognize that changes can be made in form and detail without departing from the spirit and scope of the present disclosure.

What is claimed is:

1. A method of delivering a stented prosthesis to a native heart valve; the method comprising the steps of:
providing a delivery device including:
a shaft assembly over which the stented prosthesis is compressed and secured with at least one tension member wrapped circumferentially around the stented prosthesis, the shaft assembly including at least one lumen; wherein the at least one tension member is routed through the at least one lumen;
inserting the shaft assembly and loaded stented prosthesis into a patient's vasculature; and
tensioning the at least one tension member to steer and bend a distal end of the shaft assembly.

2. The method of claim 1, further comprising the step of straightening the shaft assembly by inserting a first steering rod into the at least one lumen of the shaft assembly.

3. The method of claim 2, wherein the first steering rod has a cross-section defining a plurality of radially-extending supports.

4. The method of claim 2, wherein the step of straightening the shaft assembly includes inserting a second steering rod into a second lumen of the at least one lumen of the shaft assembly.

5. The method of claim 1, wherein the shaft assembly includes a number of outer lumens encircling a central lumen selected from the group consisting of three, four, six, eight and ten lumens; further wherein the outer lumens are symmetrically spaced about the central lumen.

6. The method of claim 1, wherein the shaft assembly includes a plurality of lumens; further wherein the lumens are asymmetrically spaced with respect to a central axis of the shaft assembly.

7. The method of claim 1, wherein the at least one tension member includes a plurality of tension members symmetrically positioned within a plurality of lumens of the shaft assembly.

8. The method of claim 1, wherein the delivery device includes an outer sheath assembly that sheathes the stented prosthesis during the step of inserting; wherein the outer sheath assembly includes a lumen in which a steering rod is inserted.

9. The method of claim 8, the at least one tension member including a plurality of tension members wherein the method further comprises the step of releasing at least some tension in the plurality of tension members after the outer sheath assembly has sheathed the stented prosthesis, prior to the step of tensioning the plurality of tension members to steer.

10. The method of claim 1, further comprising the step of releasing the at least one tension member from the stented prosthesis to release the stented prosthesis from the delivery device.

11. The method of claim 1, wherein at least one additional tension member is positioned within at least one additional lumen and is connected to a distal end of the shaft assembly; the method further comprising the step of tensioning the at least one tension member connected to the distal end to steer the distal end.

12. The method of claim 1, wherein the lumen includes a coating.

13. The method of claim 1, further comprising inserting a guide wire into one of the at least one lumen.

14. A method of delivering a stented prosthesis to a native heart valve; the method comprising the steps of:
   providing a delivery device including:
   a shaft assembly over which the stented prosthesis is compressed and secured with at least one tension member, the shaft assembly including at least one lumen; wherein the at least one tension member is routed through the at least one lumen;
   inserting the shaft assembly and loaded stented prosthesis into a patient's vasculature; and
   tensioning the at least one tension member to steer and bend a distal end of the shaft assembly, wherein the delivery device includes a release pin releasably secured to the at least one tension member; the method further comprising the step of proximally retracting the release pin to release the at least one tension member from the release pin.

15. The method of claim 14, wherein the method further comprises the step of steering the delivery device by distally moving the release pin with respect to the shaft assembly.

16. A method of delivering a stented prosthesis to a native heart valve; the method comprising the steps of:
   providing a delivery device including:
   a shaft assembly over which the stented prosthesis is compressed and secured with at least one tension member, the shaft assembly including at least one lumen; wherein the at least one tension member is routed through the at least one lumen;
   inserting the shaft assembly and loaded stented prosthesis into a patient's vasculature;
   tensioning the at least one tension member to steer and bend a distal end of the shaft assembly;
   straightening the shaft assembly by inserting a first steering rod into the at least one lumen of the shaft assembly, wherein after the step of straightening the shaft assembly, the first steering rod and the first lumen are collectively configured to prevent proximal movement of the first steering rod within the lumen.

17. The method of claim 16, wherein the lumen has a varying internal diameter.

18. The method of claim 16, wherein the lumen defines a plurality of protrusions.

19. The method of claim 16, wherein the first steering rod includes a plurality of protrusions.

\* \* \* \* \*